(12) United States Patent
Brodnick et al.

(10) Patent No.: US 7,351,208 B2
(45) Date of Patent: Apr. 1, 2008

(54) RESPIRATION MONITORING SYSTEM AND METHOD

(75) Inventors: Donald E. Brodnick, Cedarburg, WI (US); Scott R Wiese, Glendale, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 747 days.

(21) Appl. No.: 10/799,297

(22) Filed: Mar. 12, 2004

(65) Prior Publication Data

US 2005/0203431 A1    Sep. 15, 2005

(51) Int. Cl.
*A61B 5/08* (2006.01)
(52) U.S. Cl. .................................... 600/529
(58) Field of Classification Search ......... 600/529–543
See application file for complete search history.

(56) References Cited

U.S. PATENT DOCUMENTS

| | | | | |
|---|---|---|---|---|
| 4,387,722 A * | 6/1983 | Kearns | .................. | 600/529 |
| 4,630,614 A * | 12/1986 | Atlas | .................. | 600/534 |
| 4,784,162 A * | 11/1988 | Ricks et al. | .................. | 600/484 |
| 5,353,788 A * | 10/1994 | Miles | .................. | 128/204.23 |
| 5,353,793 A * | 10/1994 | Bornn | .................. | 600/386 |
| 5,824,029 A * | 10/1998 | Weijand et al. | .................. | 607/122 |
| 5,876,351 A * | 3/1999 | Rohde | .................. | 600/523 |
| 5,879,308 A | 3/1999 | Räsänen | | |
| 6,415,174 B1 * | 7/2002 | Bebehani et al. | .................. | 600/513 |
| 6,553,250 B2 * | 4/2003 | Rantala | .................. | 600/509 |
| 2002/0045836 A1* | 4/2002 | Alkawwas | .................. | 600/509 |
| 2002/0099277 A1* | 7/2002 | Harry et al. | .................. | 600/301 |
| 2004/0073127 A1* | 4/2004 | Istvan et al. | .................. | 600/513 |
| 2004/0102712 A1* | 5/2004 | Belalcazar et al. | .................. | 600/547 |
| 2006/0155354 A1* | 7/2006 | Heath | .................. | 607/142 |
| 2007/0043303 A1* | 2/2007 | Osypka et al. | .................. | 600/547 |

\* cited by examiner

*Primary Examiner*—Charles A. Marmor, II
*Assistant Examiner*—Karen E Toth
(74) *Attorney, Agent, or Firm*—Andrus, Seales, Starke and Sawall, LLP

(57) ABSTRACT

An impedance variation respiration monitor determines the variation in human body impedance between two electrodes coupled to the surface of the body. One of the two electrodes is attached to the thorax below the armpit and the other of the two electrodes is attached to the leg extending from the opposing side of the thorax. The variation in impedance between these two electrodes measured by the monitor is closely correlated to the respiration rate of the subject and is particularly responsive to and indicates combined abdominal and thoracic breathing.

24 Claims, 4 Drawing Sheets

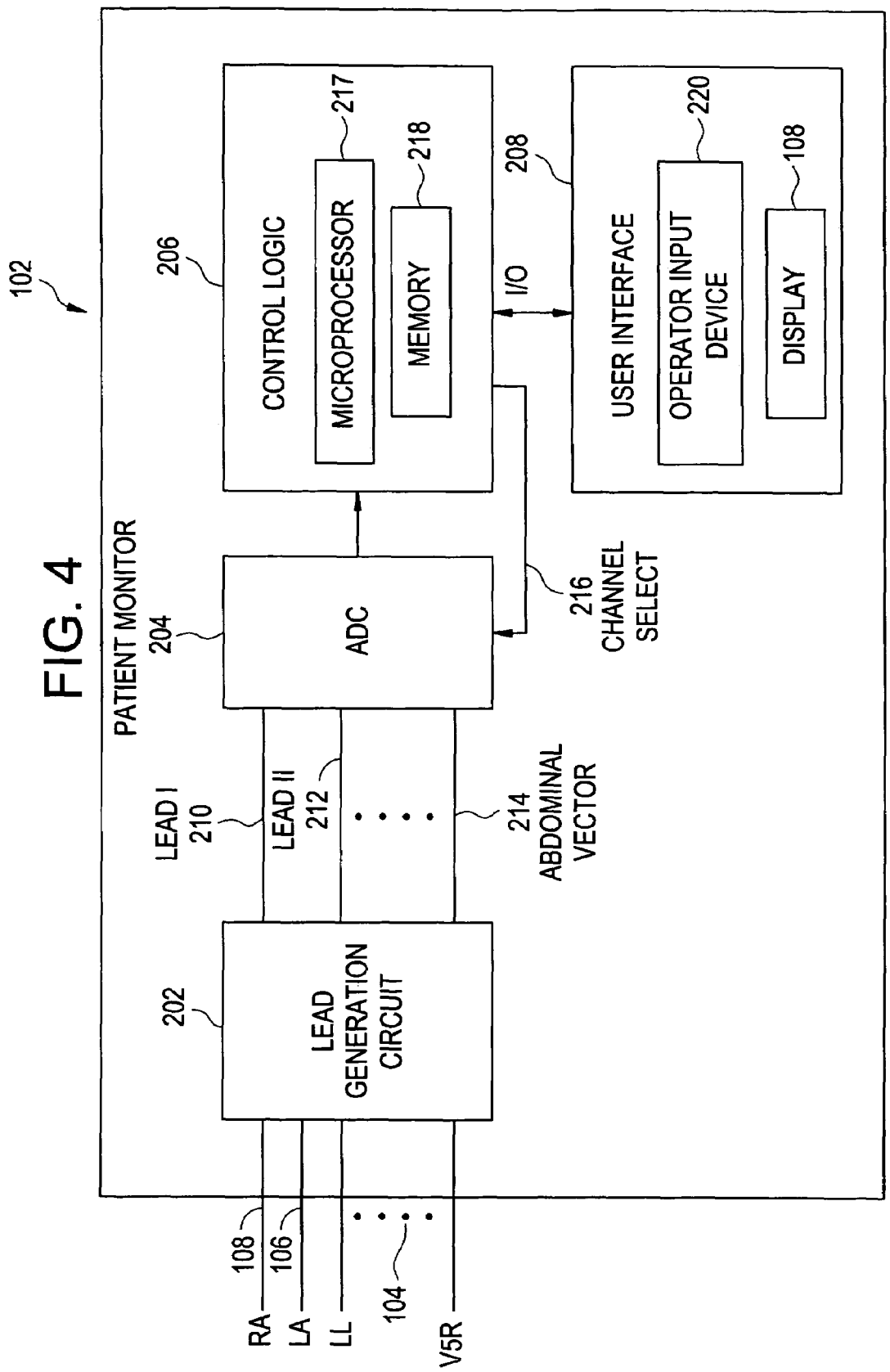

RESPIRATION MONITORING SYSTEM AND METHOD

BACKGROUND OF THE INVENTION

1. Field of the Invention

This invention relates to respiration monitoring. More particularly, it relates to respiration monitoring using impedance measuring devices connected to electrodes attached to a human body.

2. Description of the Related Art

Current respiration monitoring utilizes a technique known as impedance respiration monitoring. This technique measures the impedance between two electrodes (typically right arm and left arm) to monitor airflow. As a subject inhales, air, which is an insulator, enters the lungs and causes the net impedance in the circuit to increase. When the subject exhales, air leaves the lungs and causes the impedance in the circuit to decrease.

The current lead measurement options, i.e., leads I and II, focus on measuring thoracic breathing, which is considered a standard method of breathing in most adults. Thoracic breathing involves using the intercostals to elevate the lungs to begin inspiration. Although the chest moves significantly, only a small amount of air is actually passed into the lungs and usually only as far as the middle lobes.

Given the current leads I and II placement, which defines a conductive path across the upper portion of the thorax, left arm (LA) and right arm (RA) electrodes are well suited to measuring thoracic breathing. However, there is another more efficient type of breathing known as "abdominal breathing," which the traditional electrode placement is less effective at monitoring.

While thoracic breathing is normal in most conscious adults, children and adult subjects who relax, sleep or are otherwise unconscious, commonly adopt abdominal breathing.

Abdominal breathing occurs when the diaphragm becomes the controlling factor in the respiratory cycle. When the diaphragm controls breathing, each breath becomes deeper as more air enters the lower lobes of the lung where there is a higher concentration of blood vessels, allowing for more efficient gas exchange.

Abdominal breathing is the mode of respiration that humans use at birth because it is the most efficient. As humans grow, the conscious breathing pattern elevates to the chest to the point where we tend to forget abdominal breathing. Abdominal breathing is typical in unconscious adults. When an adult relaxes or falls asleep they will unconsciously revert back to the more efficient abdominal breathing.

As the subject transitions to abdominal breathing, the respiration signal provided by the arm electrodes is attenuated, since thoracic expansion is progressively reduced, even though the respiration is becoming more efficient. The attenuated signal could mistakenly suggest to an observer that respiration is getting worse, not better.

Thus, electrodes used to monitor respiration in their traditional ECG positions (i.e. the LA and RA electrodes) provide a respiration signal that is subject to motion artifact and is attenuated whenever the subject falls asleep. Further, the traditional placement does not indicate abdominal breathing, the dominant mode of respiration for children and unconscious adults.

What is needed therefore is a method of monitoring subject respiration that minimizes both motion artifact and cardiogenic artifact. What is also needed is a respiration monitoring method that produces a stronger signal. What is also needed is a method of monitoring respiration that would give the clinician a better option for monitoring abdominal respiration. What is also needed is a new respiration monitoring vector that will provide significant noise reduction and improved signal quality as compared to the traditional respiration monitoring vectors, i.e., leads I and II. These improvements would give clinicians more flexibility in respiration monitoring.

SUMMARY OF THE INVENTION

In one aspect of the present invention, a patient monitoring system having a plurality of inputs that is configured to be coupled to a plurality of electrodes. The plurality of electrodes includes first, second and third electrodes. A processing circuit is coupled to the plurality of inputs. The processing circuit is configured to process signals from the plurality of electrodes to produce a respiration parameter for a patient. The processing circuit has a first mode of operation in which the processing circuit produces the respiration parameter by measuring impedance between the first and second electrodes and uses the third electrode to eliminate or reduce a common mode voltage present in the signals obtained from the first and second electrodes. The processing circuit also has a second mode of operation in which the processing circuit produces the respiration parameter by measuring impedance between the third electrode and an additional one of the plurality of electrodes.

In accordance with another aspect of the present invention, an apparatus for monitoring the respiration rate of a human having a thorax and at least one lung is provided. A first input is configured to be connected to a first electrode attached to the thorax. A second input is configured to be connected to a second electrode that is attached to an opposite side of the thorax as the first electrode, and such that a conductive path extends through the human body between the first and second inputs input. A third input is configured to be connected to a third electrode. The third electrode is a RL electrode configured to eliminate or reduce a common mode voltage present in signals obtained from the first and second electrodes. A processing circuit is configured to detect fluctuations in impedance in the conductive path, and derive a respiration signal at least from the fluctuations.

According to another aspect of the present invention, a patient monitor includes a plurality of inputs that is configured to receive signals from electrodes attached to a patient. A processing circuit is configured to process the signals received from the electrodes to generate a respiration parameter relating to respiration of the patient. A display is configured to display respiration parameter and an indication that the respiration parameter provides a measurement of abdominal respiration.

According to further aspect of the present invention, a patient monitor includes an operator input device and a plurality of signal inputs that is configured to receive signals from electrodes attached to a patient. A processing circuit is configured to process the signals received from the electrodes to generate a Lead I signal, a Lead II signal, and an abdominal respiration lead signal. A display is configured to display options for selection by the operator using the operator input device, the options including an option to display a parameter associated with the abdominal respiration lead signal.

According to yet another aspect of the present invention, a method of monitoring the respiration rate of a human having an abdomen and at least one lung is provided. The method includes the steps of detecting fluctuations in impedance in a conductive path between first and second electrodes and using a third electrode to eliminate or reduce a common mode voltage present in signals obtained from the first and second electrode in a first mode of operation of a processing circuit. The first electrode and second electrode is attached to the human such that a straight line extending from the first electrode to the second electrode passes through a lower portion of the lungs adjacent to the abdomen. The method further includes detecting fluctuations in impedance in a conductive path between the third electrode and one of the first and second electrodes in a second mode of operation of the processing circuit and deriving a respiration parameter based at least on the fluctuations.

According to yet further aspect of the invention, an apparatus for monitoring the respiration rate of a human having a thorax is provided. The apparatus includes a first means for sensing body impedance configured to be fixed to the thorax. A second means for sensing body impedance is configured to be fixed to an opposite side of the thorax as the first means for sensing body impedance to thereby define a conductive path extending through the human body between the first and second means for sensing impedance. A means for monitoring respiration configured to detect fluctuations in impedance in the conductive path, and to derive a respiration signal at least from the fluctuations, the monitoring means being coupled to the first and second means for sensing and coupled via the means for sensing to the human.

BRIEF DESCRIPTION OF THE DRAWINGS

FIG. 4 is a block diagram of a patient monitor for monitoring the respiration rate of the resting subject according to an exemplary embodiment.

DETAILED DESCRIPTION OF THE PREFERRED EMBODIMENTS

Figure 1:
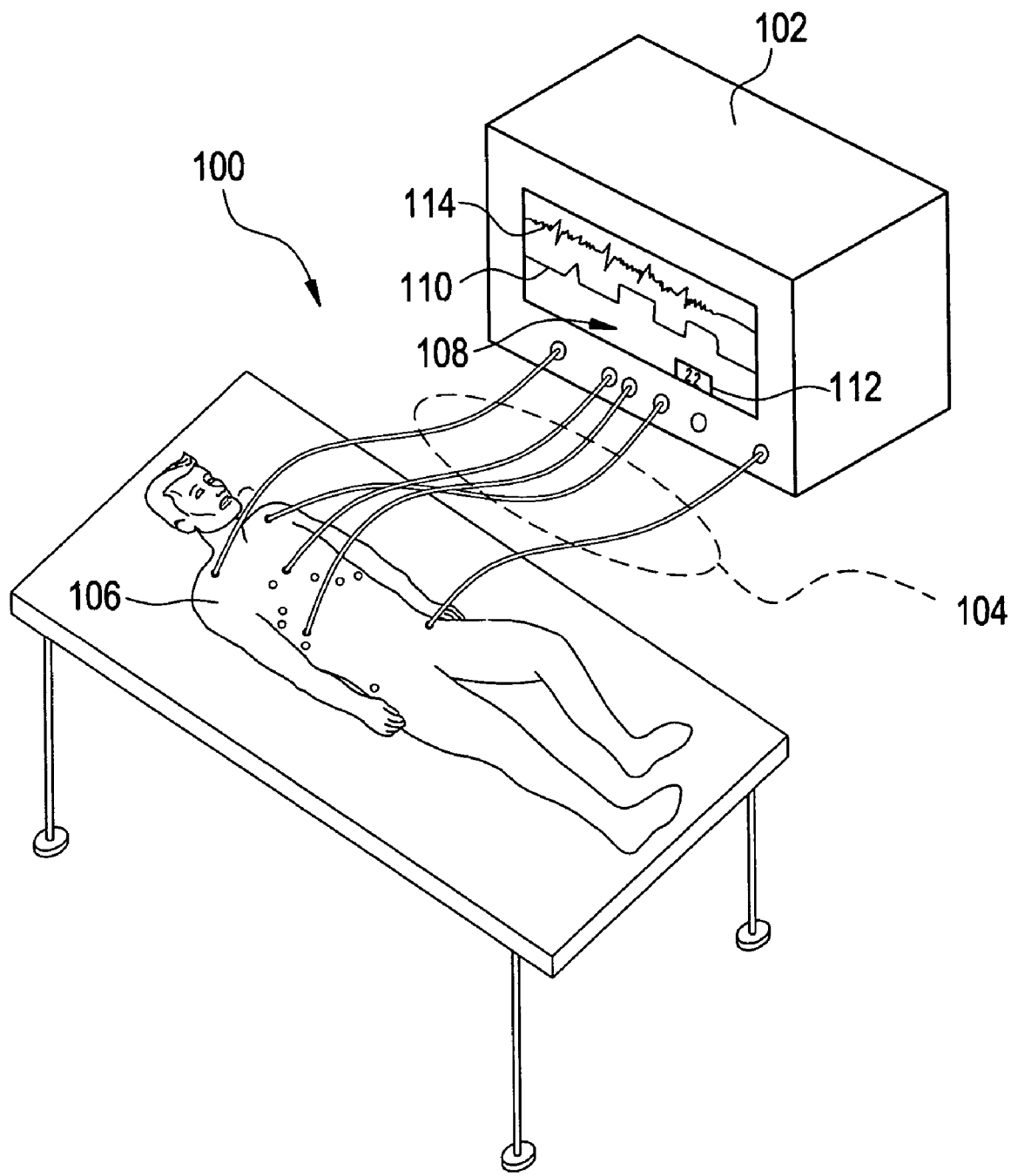
FIG. 1 is a perspective view of a resting subject connected to a combined ECG and respiration monitor by electrical leads.

FIG. 1 illustrates a respiration monitoring system 100 which includes an ECG monitor 102 and electrical lead wires 104 that are connected to monitor 102 at one end.

System 100 also includes a complete or partial subset of electrodes RA, RL, LA, LL, V1, V2, V3, V4, V5, and V6 (i.e., electrodes configured to be mounted to the subject's body at the standard RA, RL, LA, LL, V1, V2, V3, V4, V5, and V6 electrode locations), as well as one or more electrodes located at non-standard locations HV5, HV6, V5R, V6R, HV5R, and HV6R. Several of these electrodes are attached to the other end of corresponding electrical lead wires 104. Electrical lead wires 104 are connected to the monitor 102 in the illustrated embodiment. Several of these electrodes are not used for respiration monitoring purposes, but for generating ECG signals.

Monitor 102 is an impedance respiration monitor preferably having the capability of monitoring cardiac activity as well as respiration. Monitor 102 has an electronic display 108. Monitor 102 is configured to generate a respiration trace 110 on the display as well as generate a numeric indicium 112 on the display that indicates the respiration rate.

In addition to its respiration monitoring capabilities, monitor 102 is also capable of monitoring ECG signals using standard leads, including I, II, III, V, aVR, aVL, aVF, V2, V3, V4, V5, and V6. It is also capable of simultaneously analyzing leads I, II, III, and V (multi-lead mode). It should be noted that sometimes there may be no need to use all of these electrodes. And, on occasion where 4-10 electrode configurations are mounted on the subject's body, then the lead wire labeled V is permitted to be placed at any of the V (i.e., V1, V2, V3, V4, V5, V6, V7, V8, V9, V3R, V4R, and V5R) location. The standard V leads are V1 through V6. The V7 through V9 are three extra ones wrapping further around on the patient's left side. The V3R through V5R are three extra ones wrapping further around (across) the patient's right side.

Monitor 102 is configured to determine and display the subject's respiration rate by impedance variation detection—by determining changes in impedance between two of the electrodes. Monitor 102 is configured to measure the impedance between those electrodes, to track the changes in that impedance as the subject breathes, to calculate the breathing rate based upon the changes in impedance, and to display the respiration on an electronic display both as a numeric rate indicia 112 and as a trace 110 on display 108. To measure respiration, monitor 102 is responsive to a base body impedance of various ranges of ohm and frequency. For example, monitor 102 may be responsive to a 0.1 to 4000 ohm component of this impedance that varies with respiration. The rate and degree of fluctuation indicates the rate and depth of respiration.

Monitor 102 is a patient monitoring system which includes a plurality of inputs being configured to be coupled to the plurality of electrodes as noted above. The plurality of electrodes includes first, second and third electrodes. The monitor 102 includes a processing circuit that is coupled to the plurality of inputs. The processing circuit is configured to process signals from the plurality of electrodes to produce a respiration parameter for a patient. In addition, the processing circuit is capable of operating in a first mode of the operation and a second mode of the operation, simultaneously.

In the first mode of the operation, the processing circuit produces the respiration parameter by measuring impedance between the first and second electrodes and uses the third electrodes to eliminate or reduce a common mode voltage present in the signals obtained from the first and second electrodes.

In the second mode of the operation the processing circuit produces the respiration parameter by measuring impedance between the third electrode and an additional one of the plurality of electrodes. It should be noted that the monitor is configured to monitor both heart rate and breathing rate simultaneously and continuously.

Monitor 102 is further configured to have user selectable upper and lower respiration rate limits and is configured to generate an audible alarm for any respiration outside those limits.

Monitor 102 is preferably configured to simultaneously monitor ECG signals at the same time it is monitoring the subject's respiration. This arrangement is illustrated in FIG. 1, illustrating the connection of monitor 102 to the ECG electrodes and its ECG signal trace 114 on display 108. Moreover, the monitor is coupled to a hospital information system to make the information derived from the respiration signal available on the hospital information system.

The ECG circuits of monitor 102 include amplifier circuits. The electrodes receive signals generated by the heart and transmit these signals through the ECG lead wires to monitor 102. Monitor 102 amplifies and processes these signals and displays them on the monitor's display screen as traces.

The ECG circuits require a voltage reference from the subject's skin. The reference is typically provided to monitor 102 by attaching an electrode to the subject's body at the RL location and coupling that electrode to monitor 102. The voltage reference may simply provide a passive low resistance path to ground (in most ECG monitors), or it may be connected to an active circuit in monitor 102 typically called a "right leg driver."

The ECG voltage reference may also be used as one of the two variable impedance respiration monitoring connections on monitor 102.

In either case, the voltage reference electrode provides a signal to monitor 102 that permits monitor 102 to reduce or eliminate common mode noise. This common mode noise appears on the ECG electrodes that are used to provide the actual ECG signal that monitor 102 amplifies and displays.

Any electrode position described herein with an "R" appended to the end of the name has the same location as an identically named electrode location in the non-R position, but is disposed only on the opposite side of the subject's body's medial plane 116. This applies to any V electrode position. Therefore, the V5R position is even with the V5 position in the horizontal plane 117, just reflected over the medial plane 116. These "R" electrode positions are illustrated most clearly in FIG. 3.

Figure 2:
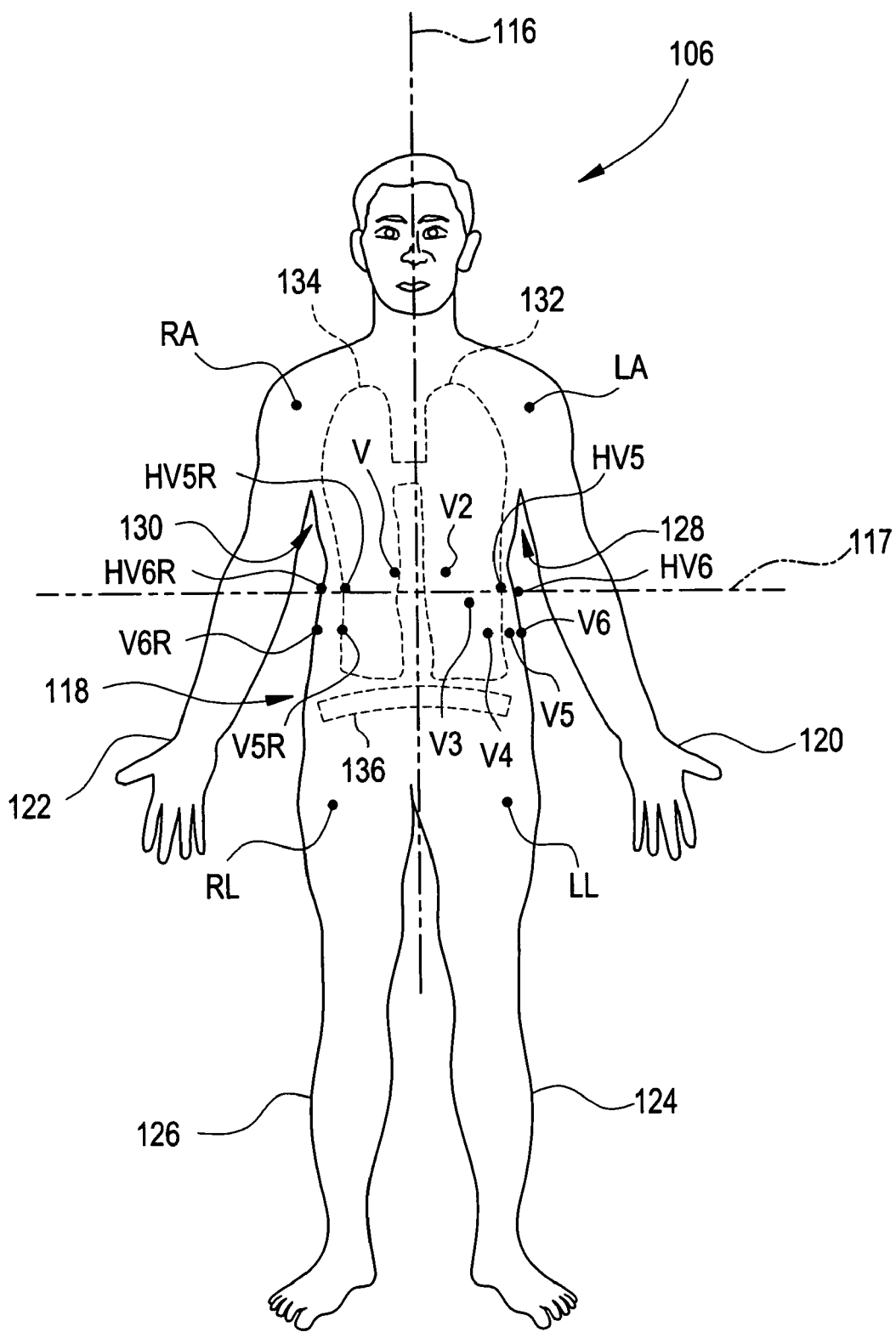
FIG. 2 is a front view of the subject's body of FIG. 1 showing the median plane, the horizontal plane, and the locations of the electrodes to which the electrical leads of FIG. 1 are connected in successive arrangements and all the electrical leads have been removed for clarity.
Figure 3:
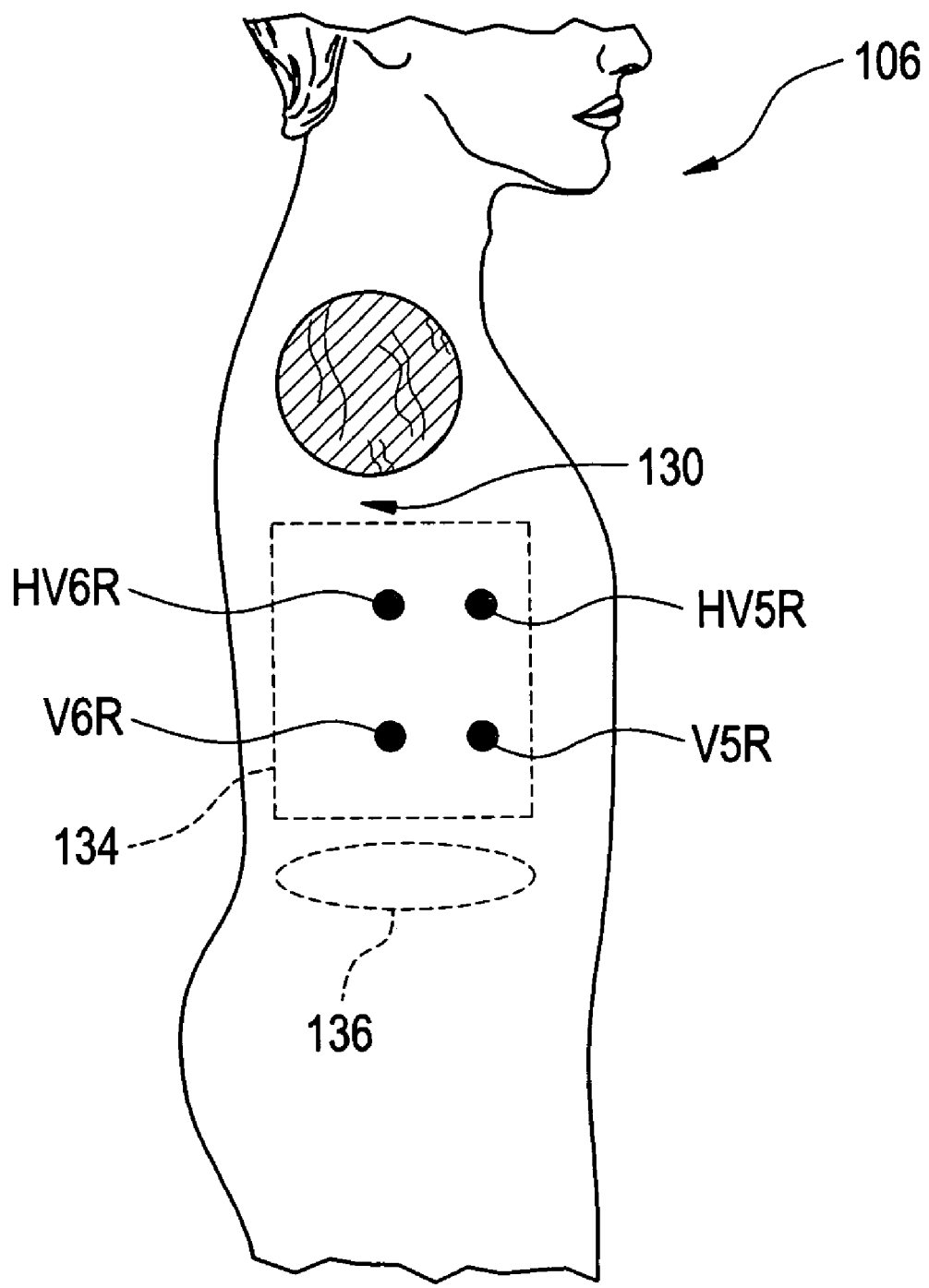
FIG. 3 is a right side view of the subject's thorax of FIGS. 1 and 2 with the right arm removed at the shoulder, and showing the positions of the V5R, V6R, HV5R and HV6R electrodes, the V5, HV5, V6 and HV6 electrode locations are located in identical positions on the left side of the subject's body, mirrored about the medial plane of the subject's body.

All the electrodes shown in FIGS. 1, 2, and 3 are preferably solid gel ECG electrodes. These electrodes are placed on the subject in 4 to 10 or more electrode configurations with the V-electrode in any of V5R through V9 or more position. When the larger leadwire set is used with the additional five lead wires labeled V2-V6, then the V should be placed in the V1 position. FIGS. 1, 2, and 3 also illustrate a number of non-standard R (right side) electrode positions as well.

FIG. 3 is a right side view of the subject's body illustrating the positions of the V5R, V6R, HV5R (high V5R) and HV6R (high V6R) electrodes. These positions are all located on the thorax generally below the right armpit.

Referring to FIG. 2, the subject 106 has a thorax 118 from which a left arm 120, a right arm 122, a left leg 124 and a right leg 126 extend. Left arm 120 defines a left armpit 128 and right arm 122 defines a right armpit 130. The subject 106 also has a left lung 132, right lung 134 and diaphragm 136.

The electrode positions are shown in detail in FIG. 3 and include High V5R (HV5R) and High V6R (HV6R) electrode positions. These positions are inline with V5R and V6R, respectively, and are located halfway between their respective standard positions (V5R and V6R) and the armpit. HV6R is in the midline of the armpit half way between the middle of the armpit and the standard V6R position. HV5R is in the midline of the armpit half way between the middle of the armpit and the standard V5R position.

Motion and cardiogenic artifact is reduced by impedance variation monitoring using a vector extending from a leg on one side of the subject's body to the subject's upper thorax on the opposing side of the body.

The first electrode is preferably located on a leg, more preferably on a leg on the side of the thorax ipsilateral (same side as) the heart, more particularly at the LL or RL locations.

The second electrode is preferably located on the upper thorax, more particularly on the upper thorax below an armpit, more particularly on the side of the upper thorax, more particularly on the side of the upper thorax below the armpit, even more particularly on the right side of the thorax at the V5R, HV5R, V6R, or HV6R locations, or alternatively on the left side of the thorax at the V5, V6, HV5, HV6 locations. Of course, non-standard positions may also be used.

The second electrode is connected not only to the respiration monitoring circuit of monitor 102, but also to the ECG voltage reference of monitor 102 to provide monitor 102 with a voltage reference signal for the ECG circuitry.

An electrode pair selected from any of the above second electrode locations and from any of the first electrode locations on the opposing side of the thorax provides superior respiration impedance monitoring. Since the second electrode is also connected to the voltage reference circuitry of the ECG circuits of monitor 102, the second electrode is selected both to provide the reference signal to the ECG circuitry and to provide one of the two impedance signals that monitor 102 uses to determine the respiration rate. This dual use of the second electrode signal permits ECG monitoring and respiration monitoring to share a common signal line (the leadwire extending between the second electrode and monitor 102) and hence reduces the total number of required connections to the subject's body.

The quality of the electrode placement is not only related to the noise response, but to the quality and strength of the average signal as well. A measurement and ranking of the standard signal strength may be used as well. This eliminates the possibility of a poor signal with no response to noise from being picked as the best.

Reference is now made to FIG. 4, which illustrates a patient monitor 102 to provide a measurement of abdominal respiration. The patient monitor 102 is equipped, among others, with a lead generation circuit 202, an analog to digital converter (ADC) 204, control logic 206, and a user interface 208. As described above in detail, four of the signal sensing electrodes, namely RA, LA, LL, and V5R are connected to the lead generation circuit 202 by standard ECG electrical lead wires 104. Additional signal sensing electrodes (not shown) may also be connected. A plurality of signal inputs are configured to receive signals from the electrodes attached to a patient. The Lead generation circuit 202 is configured to generate a Lead I signal 210, a Lead II signal 212, and an abdominal respiration lead signal 214 from the plurality of signal inputs. Leads signals 210, 212, and 214 are then converted to digital form signal by the Analog-to-digital converter (ADC) 204 and provided to control logic 206. In this arrangement, the converter 204 is a multi-channel Analog-to-digital converter (ADC) 204 which is used to select whether which lead signals (Lead I, Lead II, Abdominal Vector) is digitized and supplied to the control logic 206. A channel select signal 216 is received by the converter 204 from the control logic 206. The control logic 206 includes a conventional microprocessor 217 and a memory 218 which stores the software program that controls operation of the patient monitor 102 and stores data used in the execution of that program. Input and output circuits interface the control logic 206 to other components of the patient monitor. For example, a user interface 208 is provided which comprising an operator input device 220 (such as a control knob, a key pad, etc.) and a display 108 (such as a liquid crystal display, a cathode ray tube monitor etc.). The display 108 is configured to display respiration parameter and an indication that the respiration parameter provides a measurement of abdominal respiration.

Alternatively, the Analog-to-digital converter (ADC) 204 may be a multi-channel ADC (e.g., a separate ADC for each ECG lead) which provides data for multiple ECG leads to the control logic 206. In this configuration, the channel select signal 216 is not transmitted to the multi-channel ADC, but rather is used within the control logic 206, e.g., to determine which ECG leads are displayed by the display 108. This allows the operator to use the operator input device 220 to select a subset of the various ECG leads to be displayed. The control logic 206 and the user interface 208 cooperate to generate an image/data to be displayed by the display 108 that shows the multiple ECG waveforms selected by the operator. Other configurations, such as a time multiplexed ADC may also be used.

If the conductive path for respiration impedance monitoring is modeled as a straight line circuit extending from one electrode of the pair of electrodes to the other electrode of the pair, the most preferred electrode positions (i.e. the V5R-LL electrode positions) define a conductive path intersecting a much larger portion of the lungs than the other placements. The V5R-LL pair has the opportunity to go through two or even three lobes of the lungs. The conductive path avoids passing through the aorta and so reduces cardiogenic artifact. By having the right side terminal at V5R position instead of at the RA position, this configuration reduces the motion artifact coming from patient motion of the right arm, neck and head.

While the embodiments and application of the invention illustrated in the figures and described above are presently preferred, it should be understood that these embodiments are offered by way of example only. Accordingly, the present invention is not limited to a particular embodiment, but extends to various modifications that nevertheless fall within the scope of this application.

What is claimed is:

1. A patient monitoring system comprising:
   a plurality of inputs, the plurality of inputs being configured to be coupled to a plurality of electrodes including first, second and third electrodes;
   a processing circuit coupled to the plurality of inputs, the processing circuit being configured to process signals from the plurality of electrodes to produce a respiration parameter for a patient, the processing circuit having a first mode of operation in which the processing circuit produces the respiration parameter by measuring impedance between the first and second electrodes and uses the third electrode to eliminate or reduce a common mode voltage present in the signals obtained from the first and second electrodes, and the processing circuit having a second mode of operation in which the processing circuit produces the respiration parameter by measuring impedance between the third electrode and an additional one of the plurality of electrodes.

2. The system of claim 1, wherein the third electrode is connected to the processing circuit by the RL leadwire.

3. The system of claim 1, wherein the processing circuit is capable of operating in the first and second modes of operation simultaneously.

4. The system of claim 1, wherein the additional one of the plurality of electrodes is one of the first and second electrodes.

5. The system of claim 1, wherein the respiration parameter is respiration rate.

6. The system of claim 1, wherein the first and second electrodes are attached to a human having a abdomen and at least one lung and further wherein the first electrode and second electrodes are attached to the human such that a straight line extending from the first electrode to the second electrode passes through a lower portion of the lungs adjacent to the abdomen.

7. The system of claim 6, wherein the straight line substantially avoids passing through an aorta, heart, neck, or any shoulder of the patient.

8. The system of claim 6, wherein the first electrode is attached to at least a right or left leg.

9. The system of claim 8, wherein the first electrode is attached to the left leg at a LL location or to the right leg at a RL location.

10. The system of claim 6, wherein the second electrode is attached to an opposite side of abdomen as the first electrode and further wherein the second electrode is located below an armpit.

11. The system of claim 1, wherein the second electrode is attached to an electrode location selected from the group consisting of the V5R, HV5R, V6R, HV6R, V5, HV5, V6, and HV6 electrode locations.

12. The system of claim 11, wherein the second electrode is attached to an electrode location selected from the group consisting of the V5R V6R, HV5R and HV6R electrode locations.

13. An apparatus for monitoring the respiration rate of a human having a thorax and at least one lung, the apparatus comprising:
    a first input configured to be connected to a first electrode attached to the thorax;
    a second input configured to be connected to a second electrode attached to an opposite side of the thorax as the first electrode, and such that a first conductive path extends through a lower portion of the lungs between the first and second electrodes;
    a third input configured to be connected to a third electrode, the third electrode being a RL electrode that is configured to both eliminate or reduce a common mode voltage present in signals obtained from the first and second electrodes and provide a second conductive path with one of the first or second electrodes; and
    a processing circuit configured to detect fluctuations in impedance in the first or second conductive paths, and derive a respiration signal at least from the fluctuations.

14. The apparatus of claim 13, wherein the processing circuit is also an ECG monitoring circuit that is configured to use a signal from the third electrode as a voltage reference signal in the ECG monitoring circuit.

15. The apparatus of claim 13, wherein the processing circuit is configured to be coupled to the first electrode to at least a right or a left leg.

16. The apparatus of claim 15, wherein the processing circuit is configured to be coupled to the first electrode at the LL location or to the right leg at the RL location.

17. The apparatus of claim 13, wherein the processing circuit is configured to be coupled to the second electrode at the opposite side of thorax below the armpit.

18. The apparatus of claim 12, wherein the processing circuit is configured to be coupled to the second electrode at an electrode location selected from the group consisting of the V5R, HV5R, V6R, HV6R, V5, HV5, V6, and HV6 electrode locations.

19. The apparatus of claim 18, wherein the processing circuit is configured to be coupled to the second electrode at an electrode location selected from the group consisting of the V5R, HV5R, V6R, and HV6R electrode locations.

20. The apparatus of claim 13, wherein the processing circuit includes an electronic display screen, and further wherein the processing circuit is configured to display the respiration signal on the electronic display screen as a respiration rate numeric value.

21. The apparatus of claim 20, wherein the processing circuit is configured to display the respiration signal as a trace.

22. The apparatus of claim 21, wherein the processing circuit is configured to display the trace on the electronic display screen.

23. A patient monitor comprising:
an operator input device;
a plurality of signal inputs, the plurality of signal inputs being configured to receive signals from electrodes attached to a patient;
a processing circuit, the processing circuit being configured to process the signals received from the electrodes to generate a Lead I signal, a Lead II signal, and an abdominal respiration lead signal;
a display, the display being configured to display options for selection by the operator using the operator input device, the options including an option to display a parameter associated with the abdominal respiration lead signal.

24. A method of monitoring the respiration rate of a human having an abdomen and at least one lung, the method comprising the steps of:
detecting fluctuations in impedance in a conductive path between first and second electrodes and using a third electrode to eliminate or reduce a common mode voltage present in signals obtained from the first and second electrode in a first mode of operation of a processing circuit, the first electrode and second electrode being attached to the human such that a straight line extending from the first electrode to the second electrode passes through a lower portion of the lungs adjacent to the abdomen;
detecting fluctuations in impedance in a conductive path between the third electrode and one of the first and second electrodes in a second mode of operation of the processing circuit; and
deriving a respiration parameter based at least on the fluctuations.

* * * * *